(12) United States Patent
Ivansons et al.

(10) Patent No.: US 9,205,612 B2
(45) Date of Patent: *Dec. 8, 2015

(54) DEVICE FOR WELDING PLASTIC TUBES

(71) Applicant: Genesis BPS, LLC, Ramsey, NJ (US)

(72) Inventors: Ivars V. Ivansons, Elkton, MD (US); Dudley W. C. Spencer, Wilmington, DE (US)

(73) Assignee: Genesis BPS, LLC, Ramsey, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,008

(22) Filed: Apr. 29, 2014

(65) Prior Publication Data

US 2014/0231025 A1 Aug. 21, 2014

Related U.S. Application Data

(63) Continuation of application No. 12/481,982, filed on Jun. 10, 2009, now Pat. No. 8,708,019.

(51) Int. Cl.
*B29C 65/02* (2006.01)
*B25B 1/02* (2006.01)
*B29D 23/00* (2006.01)
*A61M 39/14* (2006.01)
*B29C 65/14* (2006.01)
*B29C 65/78* (2006.01)
*B29C 65/00* (2006.01)
*B29C 65/74* (2006.01)
*B29C 57/10* (2006.01)
*B29C 65/20* (2006.01)
*B29C 35/08* (2006.01)

(52) U.S. Cl.
CPC ........... *B29D 23/003* (2013.01); *A61M 39/146* (2013.01); *B29C 65/14* (2013.01); *B29C 65/74* (2013.01); *B29C 65/78* (2013.01); *B29C 65/7802* (2013.01); *B29C 66/1142* (2013.01); *B29C 66/5221* (2013.01); *B29C 66/8223* (2013.01); *B29C 66/82263* (2013.01); *B29C 66/857* (2013.01); *B29C 57/10* (2013.01); *B29C 65/1412* (2013.01); *B29C 65/20* (2013.01); *B29C 65/2046* (2013.01); *B29C 66/81419* (2013.01); *B29C 66/81422* (2013.01); *B29C 2035/0822* (2013.01); *B29C 2793/0081* (2013.01); *Y10T 156/1005* (2015.01); *Y10T 156/1322* (2015.01); *Y10T 156/17* (2015.01)

(58) Field of Classification Search
CPC  B29C 65/74; B29C 65/7802; B29C 65/7841; B29C 65/2046; B29C 66/857
USPC ........ 156/157, 158, 304.2, 304.5, 304.6, 503, 156/507
See application file for complete search history.

(56) References Cited

U.S. PATENT DOCUMENTS

| | | |
|---|---|---|
| 4,610,670 A | 9/1986 | Spencer |
| 4,619,642 A | 10/1986 | Spencer |
| 4,770,735 A | 9/1988 | Shaposka et al. |

(Continued)

*Primary Examiner* — Scott W Dodds
(74) *Attorney, Agent, or Firm* — Dentons US LLP

(57) ABSTRACT

A device for welding plastic tubes includes a pair of tube holders each of which has a tube clamp which includes an upper jaw and a lower jaw. The jaws in both of the tube clamps of both tube holders have smooth tube contacting walls to permit the tubing to slip through either side when the tube holders and tubes are being moved from a loading station to a stripping station to increase the length of fluid free area in the clamped tubes. A cutting/welding station provides for cutting the tubes and welding them together.

11 Claims, 2 Drawing Sheets

(56) References Cited

U.S. PATENT DOCUMENTS

| | | |
|---|---|---|
| 4,793,880 A | 12/1988 | Shaposka et al. |
| 4,832,773 A | 5/1989 | Shaposka et al. |
| 4,864,101 A | 9/1989 | Shaposka et al. |
| 4,897,138 A | 1/1990 | Shaposka et al. |
| 4,913,756 A | 4/1990 | Shaposka et al. |
| 4,929,293 A | 5/1990 | Osgar |
| 4,933,036 A | 6/1990 | Shaposka et al. |
| 5,141,592 A | 8/1992 | Shaposka et al. |
| 5,156,701 A | 10/1992 | Spencer et al. |
| 5,158,630 A | 10/1992 | Shaposka et al. |
| 5,209,800 A | 5/1993 | Spencer et al. |
| 5,244,522 A | 9/1993 | Spencer et al. |
| 5,248,359 A | 9/1993 | Shaposka et al. |
| 5,256,229 A | 10/1993 | Spencer |
| 5,279,685 A | 1/1994 | Ivansons et al. |
| 5,397,425 A | 3/1995 | Ivansons et al. |
| 5,525,186 A | 6/1996 | Ivansons et al. |
| 5,632,852 A | 5/1997 | Ivansons et al. |
| 5,674,333 A | 10/1997 | Spencer |
| 5,855,731 A | 1/1999 | Spencer |
| 5,871,612 A | 2/1999 | Spencer |
| 6,020,574 A | 2/2000 | Ivansons |
| 6,132,833 A | 10/2000 | Spencer |
| 6,177,652 B1 | 1/2001 | Ivansons |
| 6,341,637 B1 | 1/2002 | Yamada et al. |
| 6,460,592 B1 | 10/2002 | Sano et al. |
| 6,463,979 B1 | 10/2002 | Sano et al. |
| 6,637,489 B1 | 10/2003 | Spencer |
| 6,913,056 B2 | 7/2005 | Landherr et al. |
| 6,926,189 B2 | 8/2005 | Shanks et al. |
| 7,398,813 B2 | 7/2008 | Ivansons et al. |
| 8,708,019 B2 * | 4/2014 | Ivansons et al. .............. 156/503 |
| 2008/0023135 A1 * | 1/2008 | Ivansons et al. ........... 156/304.2 |

* cited by examiner

DEVICE FOR WELDING PLASTIC TUBES

CROSS REFERENCE TO RELATED APPLICATIONS

The present application is a Continuation of U.S. Nonprovisional application Ser. No. 12/481,982 filed 10 June 2009 now U.S. Pat. No. 8,708,019 issued 29 Apr. 2014, which is incorporated herein by reference in its entirety.

TECHNICAL FIELD

The present disclosure relates to devices and methods for welding plastic tubes.

BACKGROUND

Various techniques have been used for welding plastic tubes particularly as used in the medical field. U.S. Pat. No. 7,398,813 describes a device having a first tube holder and a second tube holder. Each of the tube holders has first and second parallel tube holding areas in line with each other. In practice a first tube would be placed in the aligned first tube holding areas across the location where the tube holders are adjacent each other. A second tube would be similarly placed in the aligned second tube holding areas. A tube clamp in each of the first tube holding areas clamps the first tube to create a generally fluid free area of the first tube. A tube clamp is similarly provided in the second tube holding areas to create a generally fluid free area of the second tube. At least one of the clamps is laterally movable while the clamps are maintained in their clamping condition. To increase the length of the fluid free area preferably both clamps of one of the tube holders are laterally movable by having that tube holder moved laterally. Such movement is performed after the tubes are initially loaded in a loading station, then the one tube holder is laterally moved in a stripping station to increase the size of the fluid free area. Thereafter, the tubes are cut. In U.S. Pat. No. 7,398,813 the cutting is done with a non-heated cutting device, such as a cold blade, and the tube holders are then moved to a heating station while the clamps are still maintained in their clamping condition. In the heating station a heating device heats/melts the cut stub ends of the tubes. The cut ends of the tubes are realigned so that a cut stub end of the first tube becomes aligned with a cut stub end of the second tube and these two aligned heated/melted cut stub ends are then shifted into contact with each other to become welded together.

The specific arrangement for clamping the tubes disclosed in U.S. Pat. No. 7,398,813 includes clamp jaws of different construction in one tube holder as compared with the other tube holder. More particularly the compressed tubing is held tight by square jaws in one tube holder while the jaws in the other tube holder are smooth jaws to allow the tubing to slip through the smooth jaws.

SUMMARY

An object of this invention is to provide a device for welding plastic tubes which facilitates the clamped tubing to slip through the jaws while in the clamped condition.

A further object of this invention is to modify the structure of the clamping jaws as compared to the structure disclosed in U.S. Pat. No. 7,398,813.

In accordance with this invention the clamping jaws in both of the tube holders are smooth jaws rather than one set of jaws being square jaws. This permits slippage of the tubing on either or both sides rather than holding one of the tubes tight.

DETAILED DESCRIPTION

The present invention is directed to devices for welding plastic tubes, such as disclosed in U.S. Pat. No. 7,398,813 and in the patents referred to in column 1 of U.S. Pat. No. 7,398,813. All of the details of U.S. Pat. No. 7,398,813 and the other patents referred to therein are incorporated herein by reference thereto.

Figure 1:
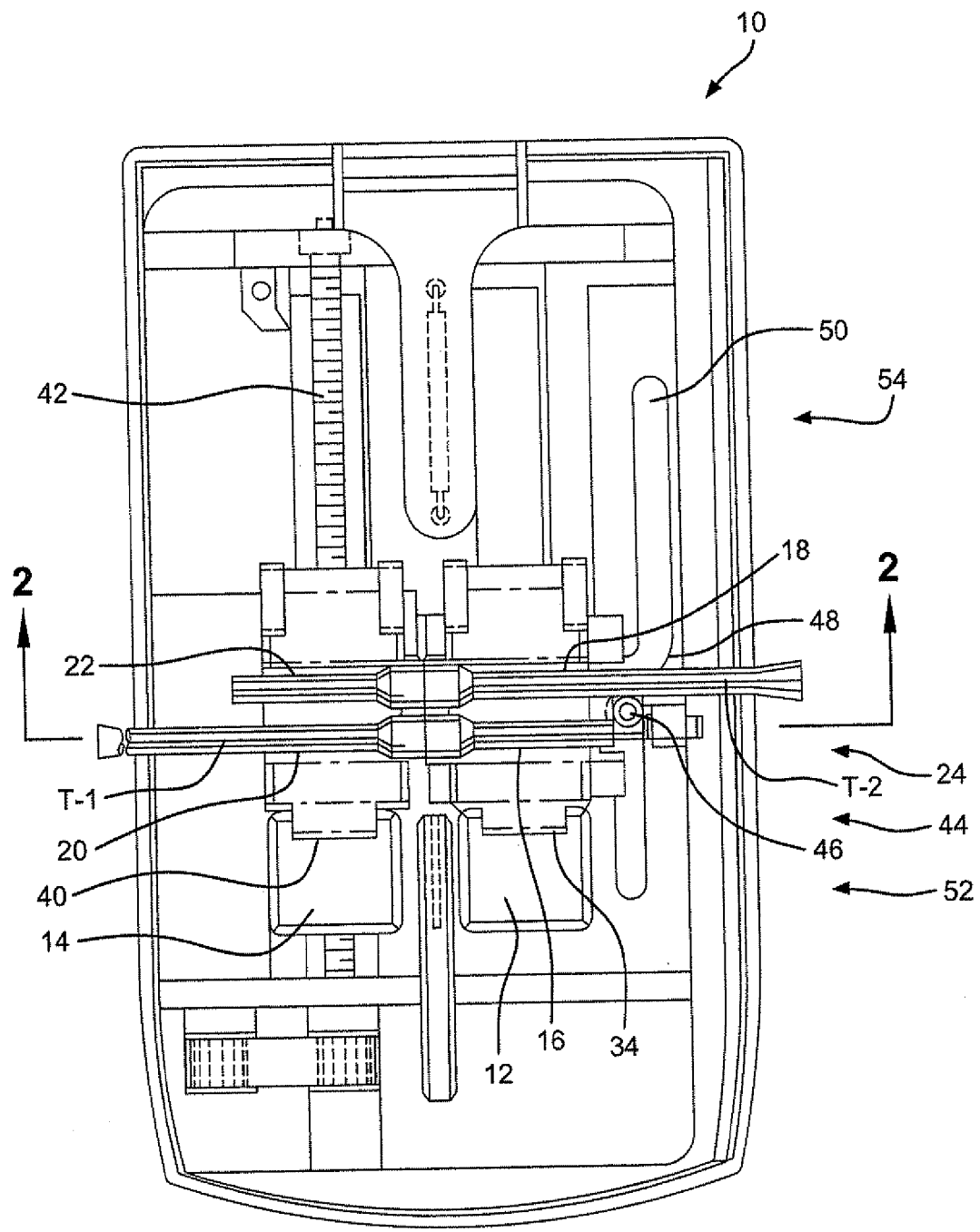
FIG. 1 is a top plan view of a device for welding plastic tubes in accordance with this invention.
Figure 2:
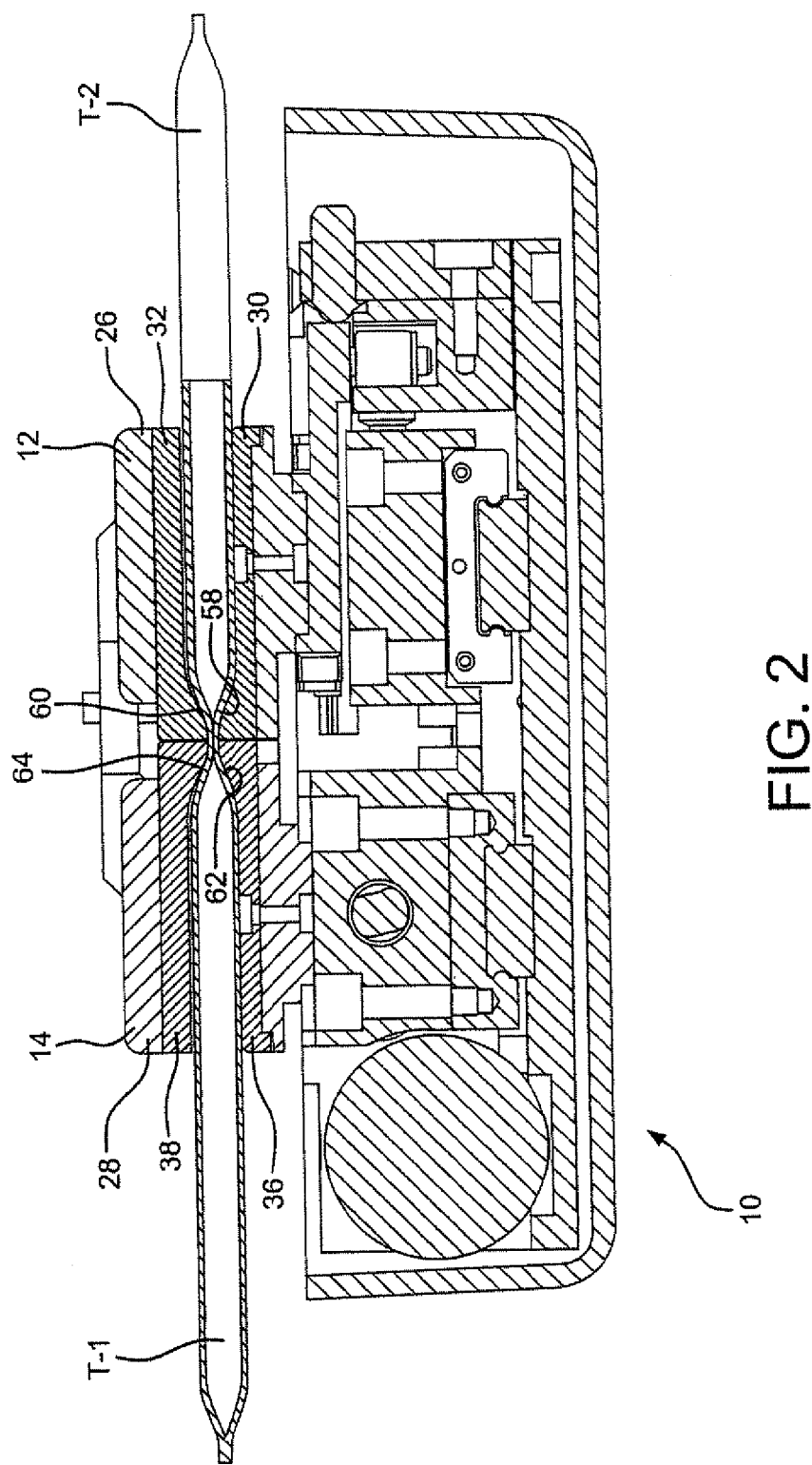
FIG. 2 is a cross sectional view taken from FIG. 1 along the line 2-2.

FIGS. 1-2 illustrate a device 10 for welding plastic tubes. As shown in FIG. 1 device 10 includes a first tube holder 12 and a second tube holder 14. Tube holder 12 includes first tube holding area 16 and a parallel second tube holding area 18. The tube holding areas may be grooves extending across the tube holder. Similarly, second tube holder 14 includes first tube holding area 20 and second tube holding area 22 which is parallel to tube holding area 20. These tube holding areas may also be grooves. The spacing between the tube holder areas 16 and 18 is the same as the spacing between tube holding areas 20 and 22.

FIG. 1 illustrates the tube holders 12 and 14 in the loading station 24 of the device 10. While in the loading station, a first tube T-1 is inserted in tube holding area 16 of tube holder 12 and in the aligned tube holding area 20 of tube holder 14. Similarly, a second tube T-2 is inserted in the aligned second tube holding areas 18 and 22. While in these tube holding areas the tubes T-1 and T-2 are clamped and held in position in each tube holder. FIG. 2 illustrates the clamping mechanism 26 for tube holder 12 and the clamping mechanism 28 for tube holder 14. The lower half of the first tube holder 12 includes tube holding areas or grooves in which are mounted a lower jaw 30. An upper jaw 32 is pivotally mounted at one end of first tube holder 12. Jaw 32 is pivoted by manipulating handle 34 to move the jaw to and from its clamped condition.

Similarly, clamp mechanism 28 for the second tube holder 14 includes a lower jaw 36 and an upper jaw 38 pivotally connected to the lower jaw 36. A handle 40 can be used to move the upper jaw into clamping relationship with the lower jaw. The tube holding areas 20,22 are also formed in the lower half of the second tube holder 14.

After the tubes T-1 and T-2 are clamped in place in the loading station 24, the tube holders 12,14 are jointly moved longitudinally by any suitable structure such as screw 42 away from the loading station 24. Such movement is controlled by cam operation. FIG. 1 illustrates a cam track 50 with two straight portions joined by curved portion 48. Cam 46 rides in track 50. The tube holders 12, 14 carrying the clamped tubes are moved together in a longitudinal direction to a stripping station 44. The cam has a slight outward bend in the track 50 that spreads the tube holders 12,14 apart at the stripping station stripping the fluid from the tubes prior to reaching a cutting blade in the cutting station 52. The carriage carrying the tube holders then reverses direction and the carriage and tube holders move completely up to the outer end of the track 50 to the heating/melting station 54. The cam 46 has a large ramp that separates the tube holders to allow them to clear the infrared heater coil and sets up the proper distance for melting. Once the melting is finished the tube holders 12,14 reverse direction and head back towards the original loading station 24 which is now the welding station. Upon passing the bend 48 the tube holders shift toward each other. One of the tube holders is held in place while the other tube holder is allowed to move longitudinally and realign the tube ends so that the two tube lines will be welded together when the clamps close laterally back together as they move pass the large ramp or bend 48 to the welding station.

The description indicated above relates to steps which are also performed in the procedures described in U.S. Pat. No. 7,398,813. In that patent, however, the jaws of the tube clamps are of a specific construction wherein the jaws for the second tube holder are specifically designed to be square jaws so that the portions of the tubes T-1 and T-2 in the second tube holder 14 are held tight by the square jaws and the tubing is allowed to slip through smooth jaws in the first tube holder 12.

FIG. 2 illustrates the tube clamps 26 and 28 to have its jaws of a form which differs from that of U.S. Pat. No. 7,398,813. In that regard, as shown in FIG. 2, the lower jaw 30 for tube holder 12 has its tube contacting wall 58 at the clamping portion to be of smooth continuous curved configuration. Similarly, the upper jaw has its tube contacting wall 60 of smooth continuous curved configuration. The jaws for second tube holder 14 have a similar construction and thus differ from the jaw construction of U.S. Pat. No. 7,398,813 which utilizes square jaws. Accordingly, as shown in FIG. 2 the lower jaw 36 has its tube clamping portion 62 to be of smooth continuous curved configuration and also has its upper jaw tube clamping portion 64 to be of smooth continuous curved configuration.

By replacing square fixed jaws with smooth radius slip jaws there is no need to hold one side of the tubing fixed. Instead, having smooth slip jaws on both tube holders 12 and 14 results in a number of distinct advantages. For example, the fluid can be stripped back from either or both sides. The tubing will slip through the side with the least resistance. In addition, very small stub ends can be made. In that regard, if hydraulic pressure in the stub end prevents the fluid from being stripped back on one side then the fluid will be stripped back on the opposite side which has less or no back pressure. Further, there is less overall tubing area to be compressed when the clamping is done with a curved radius jaw as compared to a flat jaw.

Accordingly, the jaw configurations shown in FIG. 2 represent a distinctly different jaw configuration than that previously used when moving the first tube holder laterally away from the second tube holder during a stripping action in a device for welding plastic tubes.

FIG. 1 illustrates the device 10 to have a cold cutting station 52 which is displaced from the heating station 54. The invention, however, could be practiced where both stations are combined. For example, if the tubes are cut by a heated wafer, the cutting of the tubes also results in melting the cut portions of the tubes to be in a condition for welding once the tubes are realigned and the heated ends are pressed into contact with each other.

The invention claimed is:

1. A device for welding plastic tubes comprising:
a first tube holder having first and second parallel tube holding areas;
a second tube holder having first and second parallel tube holding areas which are alignable with said tube holding areas of said first tube holder whereby a first tube may be placed in the first tube holding areas and a second tube may be placed in the second tube holding areas, said first tube holder having a first tube clamp and a second tube clamp, said second tube holder having a third tube clamp and a fourth tube clamp whereby a fluid free area is created in each of the first tube and the second tube, wherein each of said tube clamps in each of said first tube holder and said second tube holder comprises an upper jaw and a lower jaw for pressing against the respective tube between said jaws, said jaws in said tube clamps of each of said first tube holder and second tube holder having smooth tube contacting walls at their respective tube clamping portions, and each of said smooth tube contacting walls being of a smooth continuous curved configuration facilitating fluid stripping from either or both sides of the first tube and the second tube, wherein the first tube is slidably coupled to the first tube holder and the second tube is slidably coupled to the second tube holder, wherein a length of fluid free area is maintained in each of the first tube and the second tube, and each of the first tube and the second tube being slidable through a side of at least one of the first tube holder and the second tube holder with least resistance, and
a cutting/welding station to cut through the first and second tubes in a first operation and for welding portions of the tubes in a second operation.

2. The device of claim 1 wherein the cutting/welding station comprises a wafer.

3. The device of claim 2 wherein the wafer is a heated wafer.

4. The device of claim 2 wherein the wafer can be both cut and weld.

5. A device for welding plastic tubes comprising:
a first tube holder having first and second parallel tube holding areas;
a second tube holder having first and second parallel tube holding areas which are alignable with said tube holding areas of said first tube holder whereby a first tube may be placed in the first tube holding areas and a second tube may be placed in the second tube holding areas, said first tube holder having a first tube clamp and a second tube clamp, said second tube holder having a third tube clamp and a fourth tube clamp whereby a fluid free area is created in each of the first tube and the second tube, wherein each of said tube clamps in each of said first tube holder and said second tube holder comprises an upper jaw and a lower jaw for pressing against the respective tube between said jaws, said jaws in said tube clamps of each of said first tube holder and second tube holders having smooth tube contacting walls at their respective tube clamping portion, and each of said smooth tube contacting walls being of a smooth continuous curved configuration facilitating fluid stripping from either or both sides of the first tube and the second tube, wherein the first tube is slidably coupled to the first tube holder and the second tube is slidably coupled to the second tube holder, wherein a length of fluid free area is maintained in each of the first tube and the second tube, and the first tube and the second tube being slidable through a side of at least one of the first tube holder and the second tube holder with least resistance, and
a cutting/welding station to perform a first operation and a second operation.

6. The device of claim 5 wherein the first operation is a cutting operation and the second operation is a welding operation.

7. The device of claim 5 wherein the first operation and the second operation are performed by a heated element.

8. The device of claim 5 wherein the first operation is performed by a cold element and the second operation is performed by a heated element.

9. The device of claim 8 wherein the cold element and the heated element use different elements.

10. The device of claim 7 wherein the heated element is a wafer.

11. The device of claim 5 wherein the cutting/welding station has both a cold element for cutting and a heated element for welding.

\* \* \* \* \*